US008524687B2

(12) United States Patent
Conti et al.

(10) Patent No.: US 8,524,687 B2
(45) Date of Patent: *Sep. 3, 2013

(54) OPHTHALMIC PHARMACEUTICAL COMPOSITIONS BASED ON AMINO ACIDS AND SODIUM HYALURONATE

(75) Inventors: Franco Conti, Milan (IT); Francesco Saverio Dioguardi, Milan (IT); Edoardo Carlo Maria Conti, legal representative, Milan (IT); Federico Giovanni Maria Conti, legal representative, Milan (IT); Isabella Arborio Mella, legal representative, Milan (IT)

(73) Assignee: Professional Dietetics S.R.L., Milan (IT)

( * ) Notice: Subject to any disclaimer, the term of this patent is extended or adjusted under 35 U.S.C. 154(b) by 17 days.

This patent is subject to a terminal disclaimer.

(21) Appl. No.: 12/964,522

(22) Filed: Dec. 9, 2010

(65) Prior Publication Data
US 2011/0077219 A1 Mar. 31, 2011

Related U.S. Application Data

(63) Continuation of application No. 12/091,481, filed as application No. PCT/EP2006/009967 on Oct. 16, 2006, now abandoned.

(30) Foreign Application Priority Data

Oct. 26, 2005 (IT) ............................. MI2005A2036

(51) Int. Cl.
*A61K 31/715* (2006.01)
*A61P 17/02* (2006.01)

(52) U.S. Cl.
USPC .......................................................... 514/55

(58) Field of Classification Search
None
See application file for complete search history.

(56) References Cited

U.S. PATENT DOCUMENTS

| 6,645,948 | B2 | 11/2003 | Petito et al. | |
|---|---|---|---|---|
| 2002/0013359 | A1* | 1/2002 | Dioguardi | 514/423 |
| 2003/0021834 | A1* | 1/2003 | Petito | 424/445 |
| 2008/0261915 | A1 | 10/2008 | Conti | |

FOREIGN PATENT DOCUMENTS

WO     WO 03/013487 A2 *  2/2003

OTHER PUBLICATIONS

Kuchel, P.W. et al., Schaum's Outline of Theory and Problems of Biochemistry, Second Edition, "Chapter 3: Amino Acids and Peptides", relevant pp. 53-56 and 63-65, published 1998.*
Berge, S.M. et al., Journal of Pharmaceutical Sciences, "Pharmaceutical Salts", vol. 66, issue 1, pp. 1-19 (1977).*
Eastoe, J.E., The Amino Acid Composition of Mammalian Collagen and Gelatin, *Biochemical Journal*, 2a, Apr. 29, 1955, vol. 61, pp. 589-600.
Notice of Abandonment issued for U.S. Appl. No. 12/091,551, filed on Apr. 25, 2008 in the name of Professional Dietetics S.R.L.; mail date: Apr. 25, 2008.
Notice of Abandonment issued for U.S. Appl. No. 12/091,481, filed Apr. 24, 2008 in the name of Professional Dietetics S.R.L.; mail date: Apr. 24, 2008.
Notice of Abandonment issued for U.S. Appl. No. 12/091,462, filed Apr. 24, 2008 in the name of Professional Dietetics S.R.L.; mail date: Apr. 24, 2008.
Lynch, S.E. et al., Growth Factors in Wound Healing, *J. Clin. Invest.*, Aug. 1989, vol. 84, pp. 640-646.
Crowe, M.J. et al., Delayed Wound Healing in Immunodeficient TGF-β1 Knockout Mice, *The Society for Investigative Dermatology, Inc.* 2000, vol. 115, pp. 3-11.
Kay, E.P. et al., TGF-βs stimulate cell proliferation via an autocrine production of FGF-2 in corneal stromal fibroblasts, *Current Eye Research*, 1998, vol. 3 Issue 3, pp. 286-293.
Chien, Y. et al., Corneal repair by human corneal keratocyte-reprogrammed iPSCs and amphiphatic carboxymethyl-hexanoyl chitosan hydrogel, *Biomaterials*, 2012, vol. 33, pp. 8003-8016.
Byeseda, S.E. et al., ICAM-1 Is Necessary for Epithelial Recruitment of γδ T Cells and Efficient Corneal Wound Healing, *The American Journal of Pathology*, Aug. 2009, vol. 175, No. 2, pp. 571-579.
Lynch, S.E. et al., Role of platelet-derived growth factor in wound healing: Synergistic effects with other growth factors, *Proc. Natl. Acad. Sci. USA*, Nov. 1987, vol. 84, pp. 7696-7700.
Non-Final Office Action issued for U.S. Appl. No. 12/091,462, filed Apr. 24, 2008 in the name of Franco Conti; mailing date: May 28, 2010.
Notice of Abandonment issued for U.S. Appl. No. 12/091,462, filed Apr. 24, 2008 in the name of Franco Ocnti; mailing date: Feb. 23, 2011.
Notice of Abandonment issued for U.S. Appl. No. 12/091,481, filed Apr. 24, 2008 in the name of Franco Conti; mailing date: Mar. 1, 2011.
Non-Final Office Action issued for U.S. Appl. No. 12/091,551, filed Apr. 25, 2008 in the name of Franco Conti; mailing date: Jun. 10, 2010.
Notice of Abandonment issued for U.S. Appl. No. 12/091,551, filed Apr. 25, 2008 in the name of Franco Conti; mailing date: Feb. 11, 2011.
Restriction Requirement issued for U.S. Appl. No. 12/954,840, filed Nov. 26, 2010 in the name of Franco Conti; mailing date: Jan. 26, 2012.
Non-Final Office Action issued for U.S. Appl. No. 12/954,840, filed Nov. 26, 2010 in the name of Franco Conti; mailing date: Feb. 27, 2012.
Notice of Allowance issued for U.S. Appl. No. 12/954,840, filed Nov. 26, 2010 in the name ofFranco Conti; mailing date: Dec. 13, 2012.
Restriction Requirement issued for U.S. Appl. No. 12/964,419, filed Dec. 9, 2010 in the name of Franco Conti; mailing date: Mar. 13, 2012.
Non-Final Office Action issued for U.S. Appl. No. 12/964,419, filed Dec. 9, 2010 in the name of Franco Conti; mailing date: Jun. 19, 2012.

(Continued)

*Primary Examiner* — Layla Bland
*Assistant Examiner* — Bahar Craigo
(74) *Attorney, Agent, or Firm* — Steinfl & Bruno, LLP

(57) ABSTRACT

This invention relates to ophthalmic wound-healing pharmaceutical compositions based on amino acids and sodium hyaluronate.

16 Claims, No Drawings

(56) References Cited

OTHER PUBLICATIONS

Notice of Allowance issued for U.S. Appl. No. 12/964,419, filed Dec. 9, 2010 in the name of Franco Conti; mailing date: Dec. 24, 2012.
Ashcroft, G.S. et al. Topical Estrogen Accelerates Cutaneous Wound Healing in Aged Humans Associated with an Altered Inflammatory Response, *American Journal of Pathology*, vol. 155, No. 4, Oct. 1999, pp. 1137-1146.
Greenhalgh, D.G. et al., PDGF and FGF Stimulate Wound Healing in the Genetically Diabetic Mouse, *American Journal of Pathology*, vol. 136, No. 6, Jun. 1990, pp. 1235-1246.
Ashcroft, G.S. et al., Mice lacking Smad3 show accelerated wound healing and an impaired local inflammatory response, *Nature Cell Biology*, Sep. 1999, vol. 1.
El Ghalbzouri, A. et al., Fibroblasts facilitate re-epithelialization in wounded human skin equivalents, *Laboratory Investigation*, 2004, vol. 84, pp. 102-112.
Di Colandrea, T. et al., Epidermal Expression of Collagenase Delays Wound-Healing in Transgenic Mice, *Journal of Investigative Dermatoogy*, 1998, vol. 111, pp. 1029-1033.
Kapoor, M. et al., GSK-3β in mouse fibroblasts controls wound healing and fibrosis through an endothelin-1-dependent mechanism, *The Journal of Clinical Investigation*, Oct. 2008, vol. 118, No. 10, pp. 3279-.
Hu, C. et al., Basic fibroblast growth factor stimulates epithelial cell growth and epithelial wound healing in canine corneas, *Veterinary Ophthalmology*, 2009, vol. 12, No. 3, pp. 170-175.
Brown, R.L. et al., PDGF and TGF-α Act Synergistically to Improve Wound Healing in the Genetically Diabetic Mouse, *Journal of Surgical Research* 1994, vol. 56, pp. 562-570.
Unemori, E.N. et al., Interleukin-1 and transforming growth factor-alpha: synergistic stimulation of metalloproteinases, PGE2, and proliferation in human fibroblasts. *Exp Cell Res*. Feb. 1994, vol. 210, No. 2, pp. 166-171.
Lee, P-Y. et al., Electroporatic Delivery of TGF-β1 Gene Works Synergistically with Electric Therapy to Enhance Diabetic Wound Healing in db/db Mice, *J. Invest. Dermatol.*, 2004, vol. 123, pp. 791-798.
Cattaneo MG, Cappellini E, Benfante R, Ragni M, Omodeo-Salè F, Nisoli E, Borgese N, Vicentini LM Chronic deficiency of nitric oxide affects hypoxia inducible factor-1α (HIF-1α) stability and migration in human endothelial cells. *PLoS One*. 2011; 6(12):e29680. Epub Dec. 27, 2011.
Valerio A, Bertolotti P, Delbarba A, Perego C, Dossena M, Ragni M, Spano P, Carruba MO, De Simoni MG, Nisoli E. Glycogen synthase kinase-3 inhibition reduces ischemic cerebral damage, restores impaired mitochondrial biogenesis and prevents ROS production. *J Neurochem*. Mar. 2011; 116(6):1148-59. doi: 10.1111/j.1471-4159. 2011.07171.x. Epub Jan. 28, 2011.
D'Antona G, Ragni M, Cardile A, Tedesco L, Dossena M, Bruttini F, Caliaro F, Corsetti G, Bottinelli R, Carruba MO, Valerio A, Nisoli E. Branched-chain amino acid supplementation promotes survival and supports cardiac and skeletal muscle mitochondrial biogenesis in middle-aged mice. *Cell Metab*. Oct. 6, 2010; 12(4):362-72.
Tedesco L, Valerio A, Dossena M, Cardile A, Ragni M, Pagano C, Pagotto U, Carruba MO, Vettor R, Nisoli E. Cannabinoid receptor stimulation impairs mitochondrial biogenesis in mouse white adipose tissue, muscle, and liver: the role of eNOS, p38 MAPK, and AMPK pathways. *Diabetes*. Nov. 2010; 59(11):2826-36. Epub Aug. 25, 2010.
Funicello M, et al., Cathepsin K null mice show reduced adiposity during the rapid accumulation of fat stores. *PLoS One*. Aug. 1, 2007; 2(1).
de Lange P, Feola A, Ragni M, Senese R, Moreno M, Lombardi A, Silvestri E, Amat R, Villarroya F, Goglia F, Lanni A. Differential 3,5,3'-triiodothyronine-mediated regulation of uncoupling protein 3 transcription: role of Fatty acids. *Endocrinology*. Aug. 2007; 148(8):4064-72.
de Lange P, Farina P, Moreno M, Ragni M, Lombardi A, Silvestri E, Burrone L, Lanni A, Goglia F. Sequential changes in the signal transduction responses of skeletal muscle following food deprivation *FASEB J*. Dec. 2006; 20(14):2579-81.
Silvestri E, de Lange P, Moreno M, Lombardi A, Ragni M, Feola A, Schiavo L, Goglia F, Lanni A Fenofibrate activates the biochemical pathways and the de novo expression of genes related to lipid handling and uncoupling protein-3 functions in liver of normal rats. *Biochim Biophys Acta*. May-Jun. 2006; 1757(5-6):486-95.
Lanni A, Moreno M, Lombardi A, de Lange P, Silvestri E, Ragni M, Farina P, Baccari GC, Fallahi P, Antonelli A, Goglia F. 3,5-diiodo-L-thyronine powerfully reduces adiposity in rats by increasing the burning of fats FASEB J. Sep. 2005; 19(11):1552-4. Epub Jul. 12, 2005.
Silvestri E, Moreno M, Lombardi A, Ragni M, de Lange P, Alexson SE, Lanni A, Goglia F Thyroid-hormone effects on putative biochemical pathways involved in UCP3 activation in rat skeletal muscle mitochondria. *FEBS Lett*. Mar. 14, 2005; 579(7):1639-45.
De Lange P., et al., Combined cDNA array/ RT-PCR analysis of the gene expression profile in rat gastrocnemius muscle: relation to its adaptive function in energy metabolism during fasting. *FASEB J*. Feb. 2004; 18(2):350-2.
Moreno M., et al., lipid metabolism, and triiodothyronine in rat gastrocnemius muscle; interrelated roles of uncoupling protein 3, mitochondrial thioesterase, and coenzyme Q. *FASEB J*. Jun. 2003; 17(9):1112-4.
Albina et al., Temporal expression of different pathways of 1-arginine metabolism in healing wounds, *J Immunol* vol. 144, pp. 3877-3880, 1990.
Eming SA et al., Regulation of angiogenesis: Wound healing as a model, *Progress in Histochemistry and Cytochemistry*, vol. 42(3): 115-170, Dec. 10, 2007.
Frank et al., Induction of Inducible Nitric Oxide Synthase and its Coressponding Tetrahydrobiopterin-CofactorSynthesizing Enzyme GTP-Cyclohydrolase I During Cutaneous Wound Repair, The Society for Investigative Dermatology, Inc., *J Invest Dermatol* 111: 1058, 1998.
Ring BD et al., Systemically and Topically Administered Leptin Both Accelerate Wound Healing in Diabetic ob/ob Mice, *Endocrinology* vol. 141(1): 446-449, 2000.
Roberts et al., Transforming growth factor type β: Rapid induction of fibrosis and angiogenesis in vivo and stimulation of collagen formation in vitro, *Proc Nat Aced Sci* USA 83: 4167-4171, 1986.
Schwentker et al., Nitric oxide and wound repair: role of cytokines?, *Nitric Oxide* vol. 7, Issue 1, pp. 1-10, Aug. 2002.
Steed D.L., The Role of Growth Factors in Wound Healing, *Surgical Clinics of North America*, vol. 77, pp. 575-586, 1997.
Vodovotz et al., Mechanisms of Suppresison of Macrophage Nitric Oxide Release by Transforming Growth Factor β, *J Exp Med* 178: 605-613, 1993.
Witte, M.B. et al., Role of nitric oxide in wound repair, *Am J Surg*. vol. 183, pp. 406-412, 2002.
Yamasaki et al., Reversal of Impaired Wound Repair iniNOS-deficient Mice by Topical Adenoviral-mediated iNOS Gene Transfer, *J Clin Investigation, Inc.*, vol. 101, No. 5,pp. 967, 1998.
Corsetti, G. et al., R. Topic application of dressing with amino acids improves cutaneous wound healing in aged rats, *Acta histochemica*, 2010, vol. 112, pp. 497-507.
Grose R, Martin P. Parallels between wound repair and morphogenesis in the embryo. *Semin Cell Dev Biol* 10: 395-404, 1999.
Harty M, et al., Regeneration or scarring: an immunologic perspective. *Dev Dyn* 226: 268-279, 2003.
Klyce S. Electrical profiles in the corneal epithelium. *J Phisiol* 226: 407-429, 1972.
Li, D.-Q. et al., Three patterns of cytokine expression potentially involved in epithelialfibroblast interactions of human ocular surface. *J Cell Physiol* 163: 61-70, 1995.
Lu L, Reinach PS, WY Kao. Corneal epithelium wound healing. *Exp Biol and Med* 226(7). 653-664, 2001.
Nishimura T, et al., Effects of hepatocyte growth factor, transforming growth factor-beta 1 and epidermal growth factor on bovine corneal epithelial cells under epithelial-keratinocyte interaction in reconstruction culture. *Exp Eye Res* 66: 105-116, 1998.

Ueno M, et al., Accelerated wound healing of alkali-burned corneas in MRL mice is associated with a reduced inflammatory signature. *Invest Ophthalm & Visual Sci* 46 (11): 4097-4106, 2005.

Whitby DJ, et al., Rapid epithelisation of foetal wounds is associated with the early deposition of tenascin. *J Cell Sci* 99:586, 1991.

* cited by examiner

OPHTHALMIC PHARMACEUTICAL COMPOSITIONS BASED ON AMINO ACIDS AND SODIUM HYALURONATE

CROSS REFERENCE TO RELATED APPLICATIONS

The present application is a continuation of U.S. patent application Ser. No. 12/091,481 filed on Apr. 24, 2008 and incorporated herein by reference in its entirety, which is the national stage entry of PCT/EP2006/009967 filed on Oct. 16, 2006 which, in turn, claims priority to Italian Patent Application MI2005A002036 filed on Oct. 26, 2005. The present application may also be related to U.S. patent application Ser. No. 12/091,462 filed on Apr. 24, 2008, and the related continuation application Ser. No. 12/954,840 filed on Nov. 26, 2010, and to U.S. patent application Ser. No. 12/091,551 filed on Apr. 25, 2008.

FIELD OF INVENTION

The present invention relates to ophthalmic pharmaceutical compositions, based on amino acids and sodium hyaluronate, with a protective and regenerating action on the corneal epithelial cells.

PRIOR ART

No cure for hypolacrimation (dry eye) has yet been found. Dry eye syndrome is treated with eyedrops or gels (artificial tears) having a cleansing, lubricant and disinfecting action, which possess the chemico-physical characteristics of natural tears.

Artificial tears are fairly dense preparations, designed to remain in the eye at length and prevent rapid dilation.

These products considerably reduce the quality of vision after administration, and do not perform any wound-healing action.

Eye surgery designed to correct visual defects and remove cataracts is becoming increasingly common. These operations do not usually require stitches, but the wounds take some time to heal.

No wound-healing agents exist which promote rapid healing of corneal ulcerations, wounds and lesions of post-operative, pathological, traumatic or parasurgical origin.

Consequently, treatment usually involves administering topical preparations (eyedrops, ointments or artificial tears) with an antibiotic and anti-inflammatory activity.

There is therefore a need for new preparations which perform a regenerating action at epithelial level, and promote corneal re-epithelialisation and rapid healing.

DESCRIPTION OF THE INVENTION

It has now been found that the combination of some amino acids with sodium hyaluronate is particularly effective in promoting the process of reconstitution of the corneal epithelium and the stromal tissue in the case of pathological, traumatic, surgical or parasurgical corneal lesions.

The invention therefore relates to ophthalmic pharmaceutical compositions containing, as active ingredient, a combination of:
 a) glycine and proline;
 b) sodium hyaluronate; and possibly
 c) lysine and leucine.

More particularly, the compositions according to the invention contain glycine, L-proline and sodium hyaluronate, and possibly L-lysine in the form of hydrochloride and L-leucine.

The compositions according to the invention have a surprising effect as adjuvants: they aid regeneration of the epithelial microvilli and induce and accelerate corneal re-epithelialisation after eye surgery.

The compositions according to the invention will therefore be used to treat:
 slight, moderate or serious alterations of the tear film: the regeneration effect on the epithelial microvilli, which represent the fundamental substrate for effective restoration of the glycocalyx and consequently the tear film, drastically reduces the typical symptoms of dry eye.
 patients who undergo laser treatments (PRK): the reduction in post-operative re-epithelialisation time prevents the appearance of haze and dry eye syndrome which are typical of the first few months after surgery;
 relapsing and/or persistent corneal ulcers: the lasting re-epithelialisation effect prevents relapses and allows complete re-epithelialisation;
 cataract removal surgery, phacoemulsification: the rapid healing effect on the corneal tunnel significantly reduces the discomfort felt by the patient.

The compositions according to the invention will be applied to the eye 4-6 times a day, for a maximum of 3 months.

The compositions according to the invention will contain the various active ingredients within the following percentage ranges by weight:
 glycine 0.01 to 0.5%;
 L-proline: 0.09 to 0.06%;
 sodium hyaluronate: 0.5 to 0.1%
 and possibly
 L-lysine hydrochloride: 0.01 to 0.02%;
 L-leucine: 0.02 to 0.005%.

According to a preferred aspect, the compositions according to the invention will contain the various active ingredients in the following percentages by weight:
 glycine: 0.1%
 L-proline: 0.075%;
 sodium hyaluronate: 0.3%;
 and possibly
 L-lysine hydrochloride; 0.014%;
 L-leucine: 0.011%.

The following is an example of a formulation according to the invention.

EXAMPLE

| Eyedrop formulation | |
|---|---|
| INGREDIENTS | Grams per unit dose |
| Sodium hyaluronate | 0.3000 |
| L-Proline | 0.0752 |
| Glycine | 0.1000 |
| L-Lysine HCl | 0.0140 |
| L-Leucine | 0.0108 |
| Sodium chloride | 0.9000 |
| Distilled water | to 100.0 mL |

Preparation 30 kg of purified water is mixed with L-proline, glycine, lysine HCl, L-leucine and sodium chloride, and stirred until all the components have completely dissolved.

Sodium hyaluronate is added separately to 100 kg of purified water, and stirred until the component has completely dissolved.

The two solutions are combined and made up to the final volume of 144 liters with purified water, checking that the pH value is between 6 and 7, and adjusting with citric acid or sodium bicarbonate if necessary.

Finally, the solution is filtered through an 0.22 µm filter under sterile conditions and placed in a container.

Pharmacological Trial

The protective and regenerative efficacy of the artificial tears according to the invention in reconstituting the corneal epithelium and stromal tissue in the case of pathological, traumatic, surgical, or parasurgical corneal lesions was investigated.

300 eyes of 200 patients were examined:
- 100 eyes of 50 patients suffering from slight, moderate or serious alterations of the tear film (Group A);
- 80 eyes of 40 patients who underwent laser surgery (PRK) (Group B);
- 20 eyes of 20 patients suffering from relapsing and/or persistent conical ulcers (Group C);
- 84 eyes of 84 patients who underwent cataract removal surgery, namely phacoemulsification with IOL implantation (Group D).

Cytomorphological study of the eye surface with confocal scanning electron microscopy (SEM) made it possible to analyse the histological modifications of the epithelial cells, and especially the microvilli. The Schimer test and BUT were used for the staging of the tear deficiency.

Regeneration of the epithelial microvilli, the fundamental substrate for effective restoration of the glycocalyx, and consequently the tear film, was observed in Group A. The patients already perceived a noticeable benefit after 10 days of treatment, with a drastic reduction in the typical symptoms of dry eye.

In Group B, the post-operative re-epithelialisation time was shortened from the usual 4-6 days to 2-3 days, and the administration of artificial tears, even after re-epithelialisation was complete, proved to prevent the appearance of haze and the dry eye syndrome typical of the first few months after surgery.

In Group C, re-epithelialisation and stability of the epithelium were obtained, without relapses, and where the ulcer had been already present for several weeks, complete re-epithelialisation was achieved.

Early healing of the corneal tunnel, with a definite reduction in the typical discomfort felt by the patient, was observed in Group D only a few days after the cataract operation.

The invention claimed is:

1. An ophthalmic pharmaceutical composition comprising as active ingredient a combination of:
   a) glycine and proline; and
   b) sodium hyaluronate
wherein glycine, L-proline and sodium hyaluronate are comprised within the following percentage ranges by weight:
   glycine: 0.01 to 0.5%;
   L-proline: 0.06 to 0.09%; and
   sodium hyaluronate: 0.1 to 0.5%.

2. The ophthalmic pharmaceutical composition of claim 1, the composition further comprising as active ingredient:
   c) lysine hydrochloride and leucine.

3. The ophthalmic pharmaceutical composition of claim 2, wherein lysine hydrochloride is L-lysine hydrochloride, leucine is L-leucine and wherein L-lysine hydrochloride and L-leucine are comprised within the following percentage ranges by weight:
   L-lysine hydrochloride: 0.01 to 0.02%; and
   L-leucine: 0.005 to 0.02%.

4. The ophthalmic pharmaceutical composition of claim 1, wherein proline is L-proline, and wherein glycine, L-proline and sodium hyaluronate have the following percentage ranges by weight:
   glycine: 0.1%
   L-proline: 0.075%; and
   sodium hyaluronate: 0.3%.

5. The ophthalmic pharmaceutical composition of claim 2, wherein lysine hydrochloride is L-lysine hydrochloride, leucine is L-leucine and wherein L-lysine hydrochloride and L-leucine have the following percentage ranges by weight:
   L-lysine hydrochloride: 0.014%; and
   L-leucine: 0.011%.

6. The ophthalmic pharmaceutical composition of claim 1, wherein the composition is in form of eyedrops, artificial tears, ointment or gel.

7. The ophthalmic pharmaceutical composition of claim 2, wherein the composition is in form of eyedrops, artificial tears, ointment or gel.

8. The ophthalmic pharmaceutical composition of claim 3, wherein the composition is in form of eyedrops, artificial tears, ointment or gel.

9. The ophthalmic pharmaceutical composition of claim 4, wherein the composition is in form of eyedrops, artificial tears, ointment or gel.

10. The ophthalmic pharmaceutical composition of claim 5, wherein the composition is in form of eyedrops, artificial tears, ointment or gel.

11. A method to treat a corneal ulceration in a patient, the method comprising
    administering to the patient the ophthalmic pharmaceutical composition of claim 1,
    to treat the corneal ulceration in the patient.

12. A method to treat a corneal ulceration in a patient, the method comprising
    administering to the patient the ophthalmic pharmaceutical composition of claim 2, to treat the corneal ulceration in the patient.

13. A method to treat a lesion of pathological, traumatic, surgical, or parasurgical origin in a patient, the method comprising
    administering to the patient the ophthalmic pharmaceutical composition of claim 1, to treat the lesion of pathological, traumatic, surgical, or parasurgical origin in the patient.

14. A method to treat a lesion of pathological, traumatic, surgical, or parasurgical origin in a patient, the method comprising
    administering to the patient the ophthalmic pharmaceutical composition of claim 2, to treat the lesion of pathological, traumatic, surgical, or parasurgical origin in the patient.

15. A method to treat symptoms of dry eye in a patient, the method comprising
    administering to the patient the ophthalmic pharmaceutical composition of claim 1, to treat the symptoms of dry eye in the patient.

16. A method to treat symptoms of dry eye in a patient, the method comprising administering to the patient the ophthalmic pharmaceutical composition of claim 2, to treat the symptoms of dry eye in the patient.

\* \* \* \* \*